United States Patent [19]

Sanders

[11] 4,249,024

[45] Feb. 3, 1981

[54] IN SITU CONDUCTIMETRIC END POINT DETERMINATION OF THE OXYETHYLATION OF PHENOLIC COMPOUNDS

[75] Inventor: David C. Sanders, West Lafayette, Ind.

[73] Assignee: Great Lakes Chemical Corp., West Lafayette, Ind.

[21] Appl. No.: 68,710

[22] Filed: Aug. 22, 1979

[51] Int. Cl.$^3$ .............................................. C07C 41/03
[52] U.S. Cl. ................................... 568/608; 568/609; 568/610
[58] Field of Search ................ 568/608, 620, 609, 610

[56] References Cited

U.S. PATENT DOCUMENTS

| | | | |
|---|---|---|---|
| 2,331,265 | 10/1943 | Coleman et al. | 568/608 |
| 2,782,240 | 2/1957 | Hefner et al. | 568/608 |
| 3,478,111 | 11/1969 | Bruce | 568/608 X |
| 3,803,246 | 4/1974 | Rosenzweig | 568/608 |

FOREIGN PATENT DOCUMENTS 663542  5/1963  Canada.

*Primary Examiner*—Bernard Helfin
*Attorney, Agent, or Firm*—Kirkland & Ellis

[57] ABSTRACT

The present invention discloses an improved method for the in situ end point determination of the oxyethylation of phenols. In the present invention, the oxyethylation reactions occur in the presence of catalysts and at temperatures in excess of 100° C. The reaction end point is monitored by continuous measurements of the electrical conductivity of the reaction mixture and the reaction is terminated when a preselected rate of change of conductance is attained.

The method of the present invention may be used with complex phenolic systems wherein alkali metal hydroxides, quarternary ammonium salts, or alkali metal alkoxides are used as oxyethylation catalysts.

13 Claims, 5 Drawing Figures

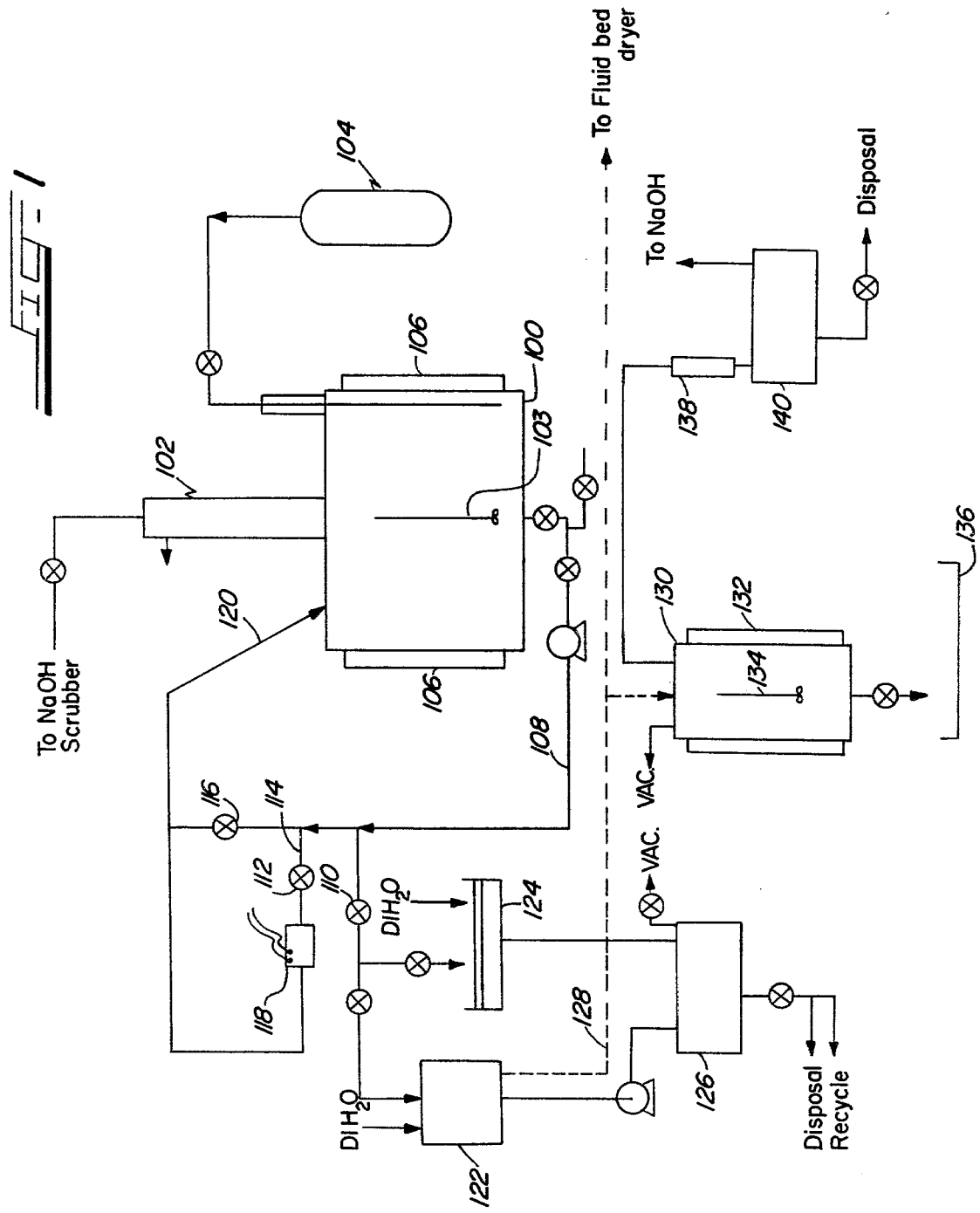

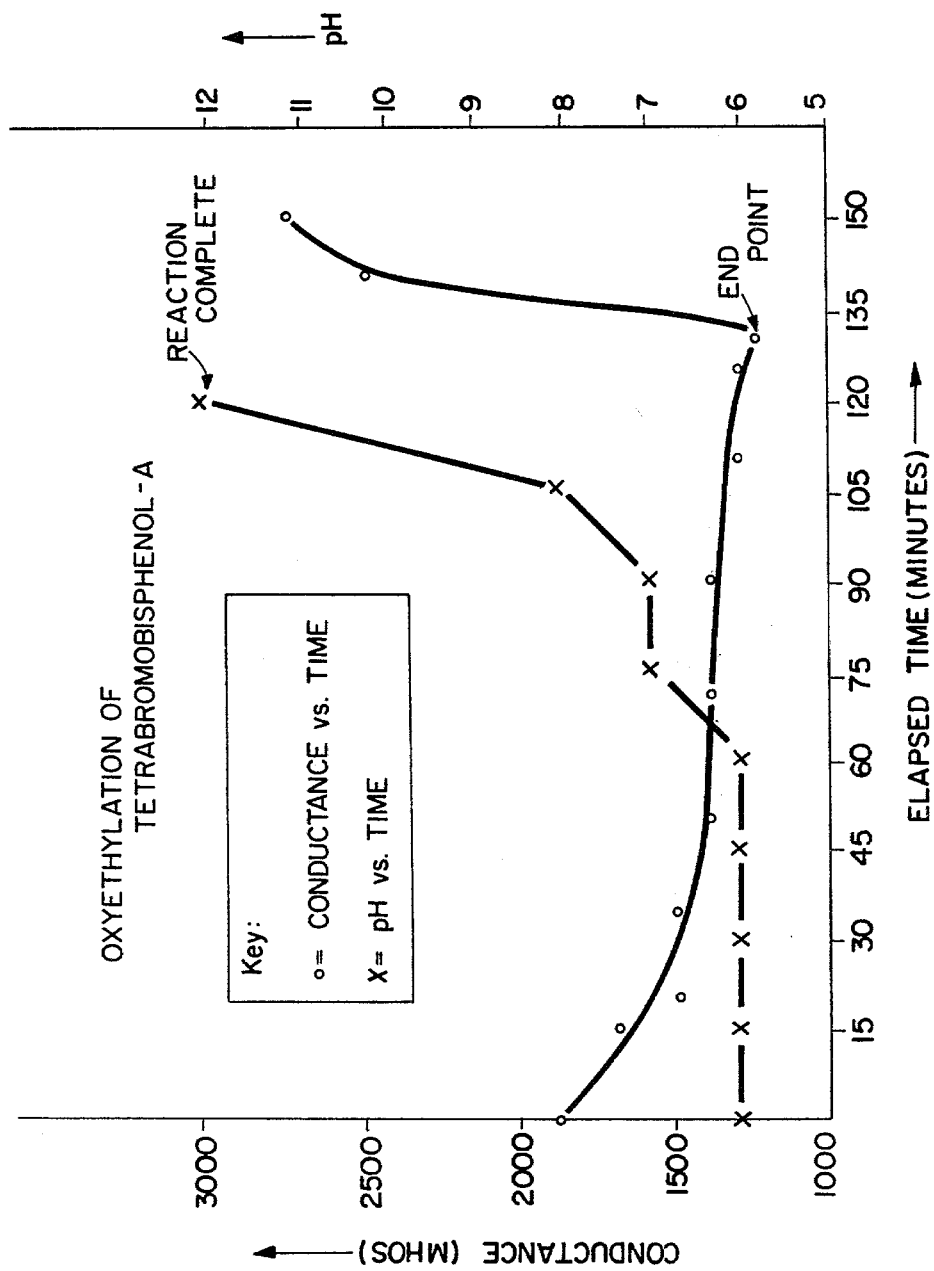

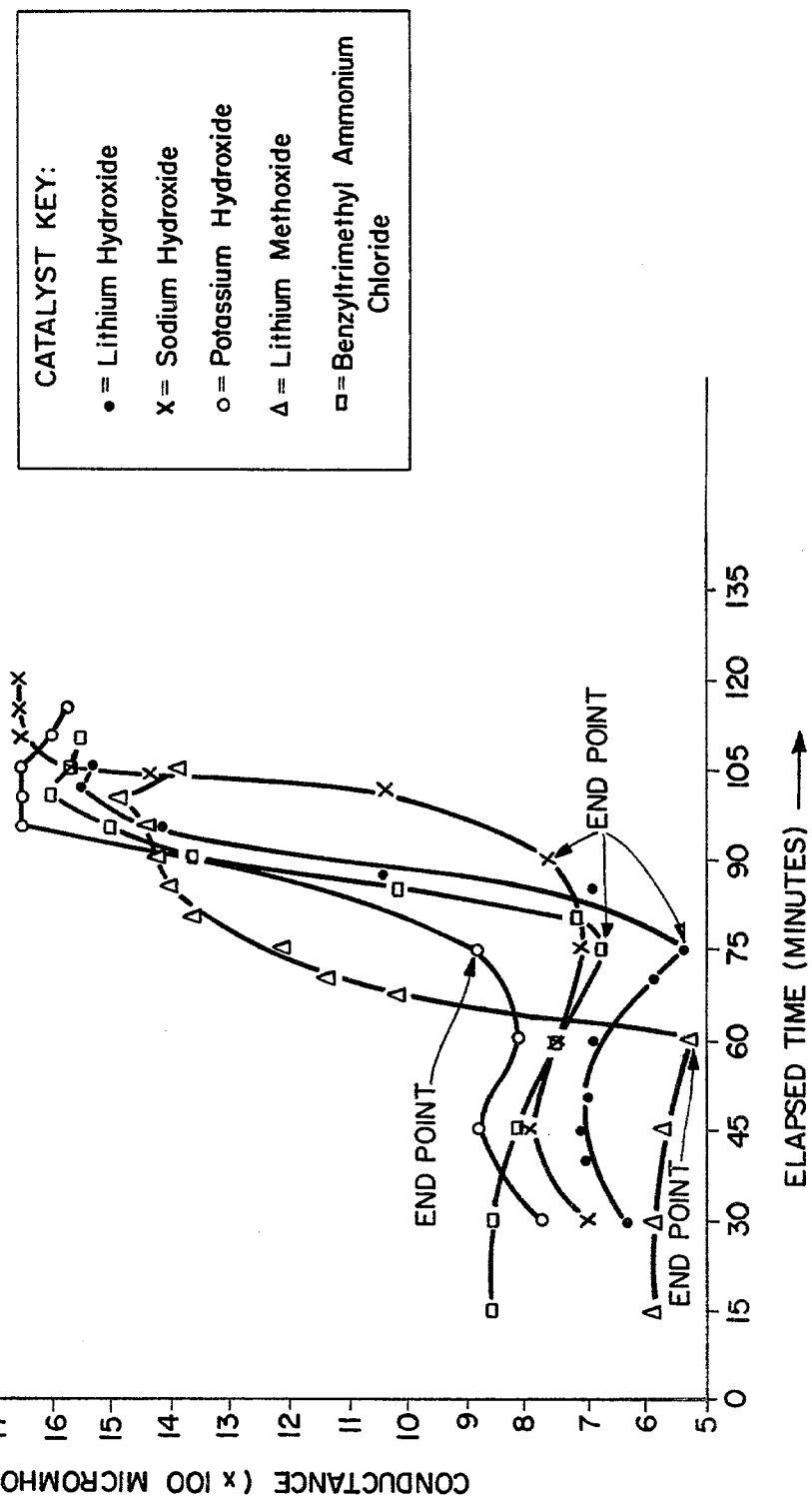

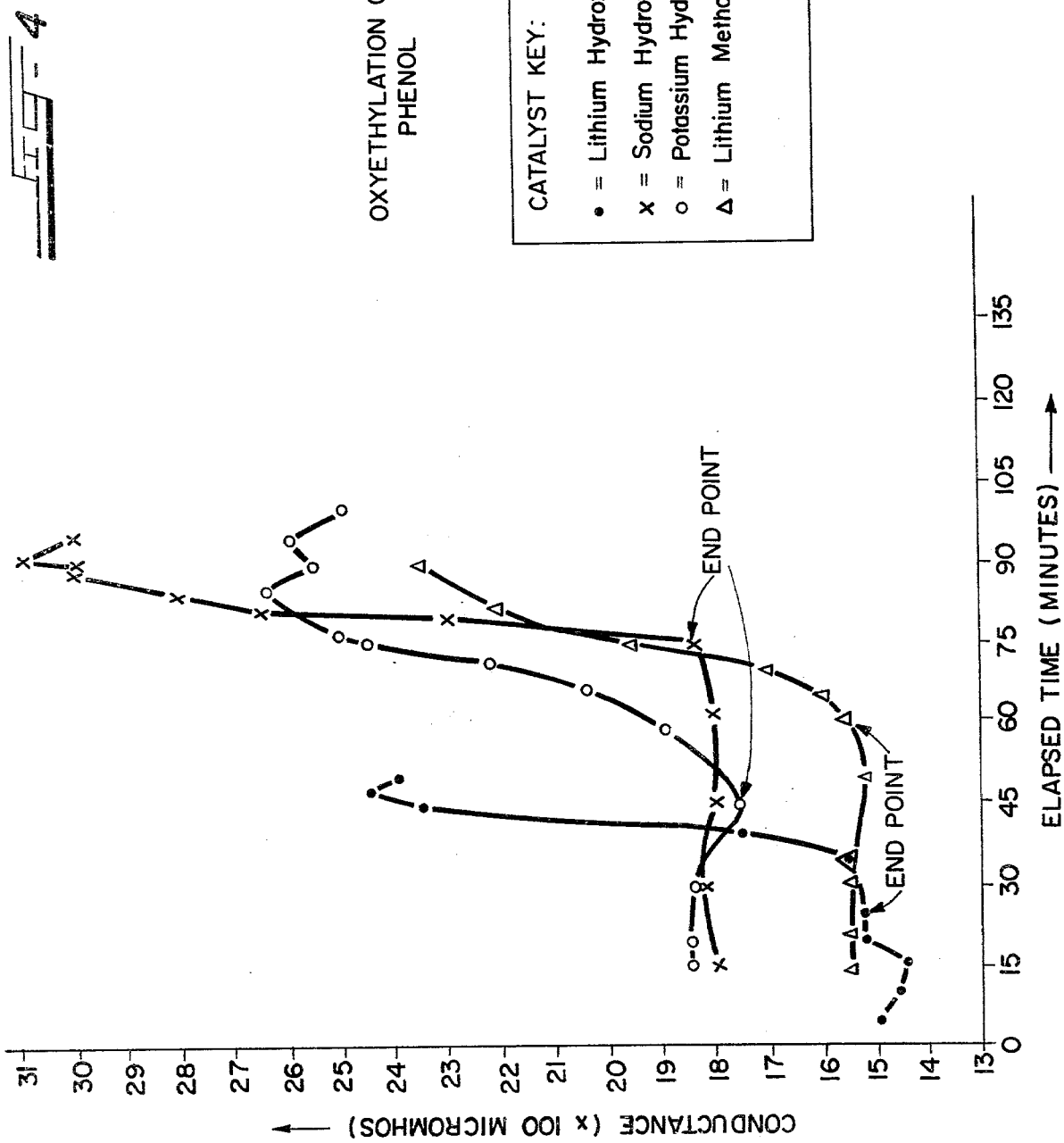

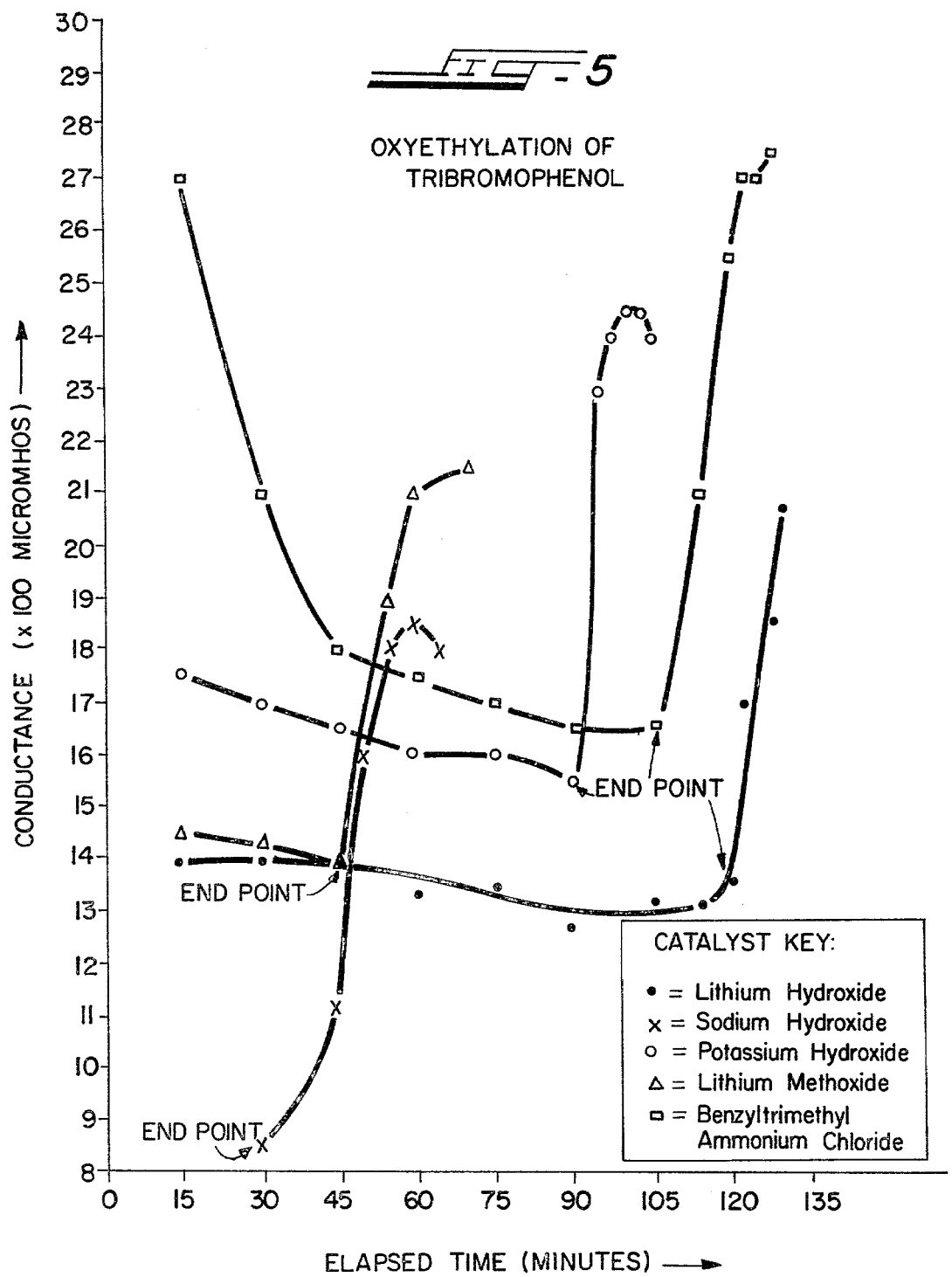

4,249,024

IN SITU CONDUCTIMETRIC END POINT DETERMINATION OF THE OXYETHYLATION OF PHENOLIC COMPOUNDS

BACKGROUND OF THE INVENTION

This invention relates generally to the catalytic oxyethylation reaction of phenols at temperatures in excess of 100° C. and more particularly to an improved method for the in situ detection of the substantial end point of such reactions.

DESCRIPTION OF THE PRIOR ART

There are several well-known methods for preparing oxyethylated derivatives of phenols. These generally comprise the reaction of an alkylene oxide, such as ethylene oxide, in the presence of an alkaline catalyst with an organic compound containing a hydroxyl group, such as an alcohol or a phenol. For example, U.S. Pat. 3,803,246 discloses a process for the oxyalkylation of diphenols at temperatures ranging from 100° C. to 200° C. Similarly, U.S. Pat. No. 2,331,265 discloses a method of etherifying bisphenols by reacting bisphenols with an alkylene oxide, such as ethylene oxide, at a reaction temperature of between 125° C. and 170° C., with or without a catalyst such as sodium hydroxide.

However, these and other similar prior art references make no mention of the need for reaction end point detection. Such detection is critical in most instances since process time and reactants may be conserved and product quality controlled when the end point is known. Also, the reaction may be terminated before detrimental effects, such as thermal decomposition or degradation, occur to the reaction products. For example, it is known that tetrabromobisphenol A of the formula

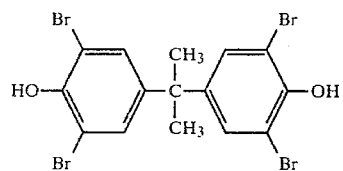

may be advantageously used as a precursor to the manufacture of additive or reactive flame retardants for use in polyester-forming reactions. Such materials may be prepared through oxyethylation reactions. However, in order to achieve desirable high thermal stability without undesirable color being imparted to the final polyester product, it is necessary to closely monitor the system in which the materials are produced. Oftentimes competing factors must be weighed in the production of such materials. Thus, while a more efficient reaction process may occur at a higher temperature, the higher reaction temperature may adversely affect properties such as purity, color, and flame retardance. Likewise, prolonged exposure of the reactive product to a lower temperature may cause undesirable color generation in the material although the thermal stability thereof may not be adversely affected.

These competing factors make it necessary to closely monitor the on-going reaction in order to determine the substantial end point thereof. It has long been recognized that pH measurements may be useful in monitoring reaction end-points. However, such pH monitoring for catalytic oxyethylation of phenols is complicated by the fact that the reaction temperatures generally preferred are in excess of 100° C. Thus, the use of a common pH electrode in the reaction vessel (or stream) is inefficient since the electrodes rapidly deteriorate upon exposure to temperatures in this range. Such deterioration precludes the use of pH electrodes in continuous or large scale batch processing. Likewise, although the use of simple "pH strips" may provide an indication of reaction end point, such manual operation is clearly not readily adaptable for pilot plant or full-scale plant operations. Thus, pH measurements as a method for the in situ monitoring of the end point of the catalytic oxyethylation of phenols is impractical.

SUMMARY OF THE INVENTION

The above-noted, and other, shortcomings of the prior art are overcome by the present invention. In particular, the present invention provides a method for the in situ detection of the substantial end point of the oxyethylation of phenols by measuring the conductivity of the reaction mixture continuously during the reaction. As the reaction proceeds to completion, conductance changes gradually until end point is reached at which time the conductance exhibits a significant increase over a relatively short period of time. Thus, by providing an in-line conductrimetric measurement device in the pilot or full-scale plant, it is possible to routinely and accurately determine the substantial end points of phenolic oxyethylation reactions.

Accordingly, it is an object of the present invention to provide a method for the in situ monitoring of the oxyethylation of phenols in order to establish the end point of such reactions.

It is a further object of the invention to utilize conductimetric monitoring of the catalytic oxyethylation of phenols in temperature regimes in excess of 100° C. in order to establish reaction end point.

It is yet still another object of the invention to provide a conductimetric method for the in situ end point monitoring of the catalytic oxyethylation of phenols which is readily adaptable to pilot plant and full-scale plant operation.

BRIEF DESCRIPTION OF THE DRAWINGS

The foregoing and other objects of the present invention will be more fully understood by reference to the following detailed description and the appended drawing of which:

FIG. 1 is a schematic of a typical pilot plant set-up for the catalytic oxyethylation of phenols;

FIG. 2 is a graphic compilation of conductance versus elapsed time and pH versus elapsed time for the addition of ethylene oxide to tetrabromobisphenol A;

FIG. 3 is a composite graph of conductance versus elapsed reaction time for the oxyethylation of tetrabromobisphenol A using different catalysts;

FIG. 4 is a composite graph of conductance versus elapsed reaction time for the oxyethylation of phenol using different catalysts;

FIG. 5 is a composite graph of conductance versus elapsed reaction time for the oxyethylation of tribromophenol using different catalysts.

DETAILED DESCRIPTION OF THE INVENTION

The oxyethylation of phenols in the presence of catalysts is subject to a number of mechanistic interpretations. For example, when the catalyst is a strong base, such as, for example, an alkali metal hydroxide, the mechanism may be described as a two step nucleophilic substitution ($S_N2$), where phenoxide acts as the nucleophile:

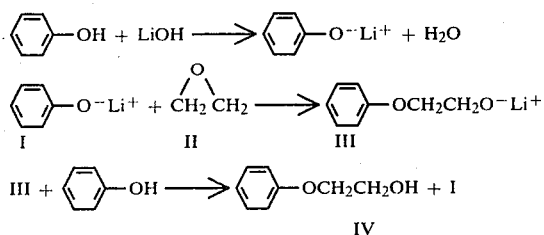

at end point:
III + H₂O → IV + LiOH

On the other hand when the catalyst is a quaternary ammonium salt (such as benzyltrimethylammonium chloride, which for the present purposes is abbreviated as "R+X−"), a complex mechanism may describe the oxyethylation process:

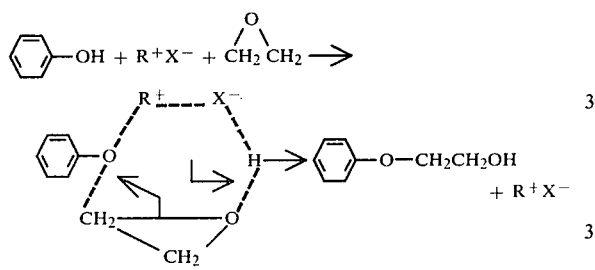

Whatever reaction mechanism may be proposed for the oxyethylation of phenols, it has been discovered that as the reaction nears end point a marked and unexpected increase in the electrical conductivity of the reaction mixture occurs over a relatively short time. This increase has been noted in reaction systems where immediately prior to end point the conductance had been decreasing and also in systems where, prior to end point, the conductance had been increasing. Thus, it is the dramatic conductance increase which forms the basis of the method of present invention.

In order to more fully appreciate the nature and effect of the present invention, reference is made to FIG. 1 which is a schematic of a typical pilot plant set up for the oxyethylation of phenols. For the purposes of the present invention the term "phenol" and "phenolic" includes those organic compounds containing a hydroxyl group attached to an aryl substrate such as, for example, hydroxybenzene (more commonly referred to as phenol); halophenols such as, for example, bromophenol, chlorophenol, and tribromophenol; and diphenols and halodiphenols such as, for example. 4,4' dihydroxybiphenyl, 3-bromo-4,4'-dihydroxybiphenyl, hydroquinone, bisphenol A, and tetrabromobisphenol A, etc.

As noted in FIG. 1, the reactants are charged into a reaction vessel 100, which is provided with a condenser column 102 and agitator 103. Ethylene oxide may be controllably added to the vessel 100 from storage tank 104. In order to control the temperature of the reaction, a steam jacket 106 encircles the vessel 100. During the reaction, a stream of reaction solution is continuously withdrawn from the vessel 100 through a line 108 and may be directed through line 114 when valves 110 and 116 are closed and valve 112 is open. Positioned in the line 114 is a conductimetric cell 118 which measures the conductance of the reaction solution (recording devices for the cell 118 are not shown). The reaction solution is then directed through a return line 120 back to the reaction vessel 100. When the conductance measurements establish that reaction end point has been achieved the valve 112 is closed and the valve 110 is opened thus allowing withdrawal of product. The product may then be variously directed through centrifuge 122 or filter 124 for centrifugation or filtration. The desired product, withdrawn from centrifuge 122 may be removed to a fluid bed dryer (not shown) or, through line 128, to a water strip reactor 130, where water is removed from the product. Thereafter, the product is transferred to receiver 140.

With this brief description of a typical pilot plant operation, it can be noted that on-line measurement of the reaction process can be readily achieved by positioning the conductimetric cell 118 within the flow of the processing plant.

In order to establish the viability of using conductimetric measurements to determine reaction end point, a series of examples are presented.

EXAMPLE I

Tetrabromobisphenol A ("TBBPA"), 136 g, 0.25 moles, of the formula

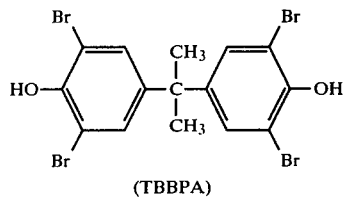

(TBBPA)

is slurried with 250 g of ethylene glycol in the reactor. The vessel is fitted with a dry-ice condenser, agitator, and a sub-surface gas inlet tube for introduction of ethylene oxide. A platinum electrode, which is immersed in the reaction mixture, is externally attached to a conductance meter. The mixture is heated to 100° C. and lithium hydroxide monohydrate (1.0 g, 0.024 moles, 0.74% w/w of TBBPA) is added. Ethylene oxide (25 g, 0.57 moles) is added, subsurface, continuously over a two hour period. After approximately 10% of the ethylene oxide is added, the reaction mixture changes from a slurry to a clear yellow to light green solution. The solution color fades as the reaction proceeds.

The conductance of the reaction mixture is measured continuously and recorded at frequent time intervals. Conductance data are presented in Table I and FIG. 2. At the completion of the reaction, the product is removed, washed, dried, and analyzed.

TABLE I

| Time (minutes) | Reaction Temperature, °C. | Conductance (Mhos) |
|---|---|---|
| 0 | 118 | 1900 |
| 15 | 118 | 1700 |
| 20 | 118 | 1500 |
| 35 | 118 | 1500 |
| 50 | 118 | 1400 |
| 70 | 118 | 1400 |

TABLE I-continued

| Time (minutes) | Reaction Temperature, °C. | Conductance (Mhos) |
| --- | --- | --- |
| 90 | 118 | 1400 |
| 110 | 117 | 1300 |
| 125 | 118 | 1300 |
| 130 | 118 | 1250 |
| 140 | 118 | 2500 |
| 150 | 118 | 2800 |

As can be noted from Table I and FIG. 2 a dramatic conductance change occurs between 130 and 140 minutes of elapsed reaction time. Analysis of the product indicates that 99+% of the TBBPA was converted to bis(2-hydroxyethyl ether) of tetrabromobisphenol A of the formula

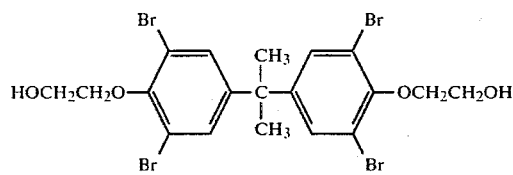

EXAMPLE II

Example I is repeated except that 0.2 ml samples of the reaction mixture are withdrawn every 15 minutes and the pH thereof is measured using pH strips. No conductance measurements are recorded. Table II and FIG. 2 present pH versus elapsed reaction time (in minutes) data. As there observed, the reaction end point is reached after about 120 minutes of reaction time as evidenced by the rapid increase in basicity of the reaction mixture. Analysis confirms that 99+% of bis(2-hydroxyethyl) of TBBPA is formed. It is noted that the pH determination of reaction end point compares favorably to that determined by conductance in Example I.

TABLE II

| Time (minutes) | pH |
| --- | --- |
| 0 | 6 |
| 15 | 6 |
| 30 | 6 |
| 45 | 6 |
| 60 | 6 |
| 75 | 7 |
| 90 | 7 |
| 105 | 8 |
| 120 | 12 |

EXAMPLE III

A series of experiments are performed similar to Example I except that 350 g of the ethylene glycol is used and the amount of ethylene oxide added to end point is measured. In this Example, the catalyst and the amount thereof is varied.

Table III presents the combinations of materials used in this Example III.

TABLE III

| Phenolic | Catalyst | Ethylene Oxide To End Point |
| --- | --- | --- |
| Tetrabromobis-phenol A, 136g (0.25 moles) | Lithium hydroxide hydrate, 1g. | 25.0g |
| | Sodium hydroxide, 1g. | 24.5g |
| | Potassium hydroxide, 1g. | 25.5g. |
| | Lithium methoxide, 1g. | 25.0g. |
| | Benzyltrimethyl- | 27.0g. |

TABLE III-continued

| Phenolic | Catalyst | Ethylene Oxide To End Point |
| --- | --- | --- |
| | ammonium chloride, 8.3g | |

A summary of the conductance measurements for these reactions is presented in Table IV.

TABLE IV

Conductance measurements for oxethylation of tetrabromobis-phenol-A (× 100 micromhos)

| CATALYST | TIME (Min.) | | | | | | | |
| --- | --- | --- | --- | --- | --- | --- | --- | --- |
| | 0 | 15 | 30 | 45 | 60 | 75 | 90 | 105 |
| Lithium Hydroxide | — | — | 6.4 | 7.2 | 6.9 | 5.4* | 13.6 | 15.3 |
| Sodium Hydroxide | — | — | 7.0 | 8.0 | 7.5 | 7.2 | 7.6* | 15.7 |
| Potassium Hydroxide | — | — | 7.8 | 8.7 | 8.2 | 8.9* | 13.6 | 16.5 |
| Lithium Methoxide | — | 5.9 | 5.9 | 5.7 | 5.3* | 12.3 | 14.2 | 13.8 |
| Benzyltrimethyl-Ammonium Chloride | — | 8.6 | 8.6 | 8.2 | 7.5 | 6.7* | 13.6 | 15.7 |

*Reaction End Point

The conductance measurements for this Example III are plotted in FIG. 3 and show the dramatic effect on conductance which occurs when reaction end point is reached.

EXAMPLE IV

A second series of experiments are run similar to Example I. However, 23.53 g of phenol and 350 g of ethylene glycol are used and the amount of ethylene oxide added to end point is measured. Table V presents the catalysts and amounts of ethylene oxide.

TABLE V

| Phenolic | Catalyst | Ethylene Oxide To End Point |
| --- | --- | --- |
| Phenol, 23.53g | Lithium hydroxide, 1g | 12.6g |
| | Sodium hydroxide, 1g | 13.0g |
| | Potassium hydroxide, 1g | 12.0g |
| | Lithium methoxide, 1g | 12.5g |

A summary of the conductimetric data measured for this Example IV is presented in Table VI.

TABLE VI

Conductimetric measurements for the oxyethylation of phenol (× 100 micromhos)

| CATALYST | TIME (Min.) | | | | | | |
| --- | --- | --- | --- | --- | --- | --- | --- |
| | 0 | 15 | 30 | 45 | 60 | 75 | 90 |
| Lithium Hydroxide | — | 14.0 | 15.4* | 23.5 | | | |
| Sodium Hydroxide | — | 18.0 | 18.3 | 18.0 | 18.0 | 18.3* | 30.0 |
| Potassium Hydroxide | — | 18.5 | 18.5 | 17.5* | 19.0 | 24.5 | 25.5 |
| Lithium Methoxide | — | 15.5 | 15.5 | 15.4 | 15.5* | 19.7 | 23.5 |

*Reaction End Point

The conductance measurements for this Example IV are plotted in FIG. 4 which again shows the dramatic increase in conductance when end point is reached.

EXAMPLE V

A third series of examples is run similar to Example I except that 82.7 g of tribromophenol and 350 g of ethylene glycol are used and the amount of ethylene oxide added to end point is measured. The catalysts are varied as noted in Table VII.

TABLE VII

| Phenolic | Catalyst | Ethylene Oxide Added To End Point |
|---|---|---|
| Tribromophenol, 82.7g | Lithium Hydroxide, 1g | 13.0g |
| | Sodium Hydroxide, 1g | 12.5g |
| | Potassium Hydroxide, 1g | 12.5g |
| | Lithium Methoxide, 1g | 13.5g |
| | Benzyltrimethyl-Ammonium Chloride, 8.3g | 13.0g |

A summary of the conductimetric data measured for this Example V is presented in Table VIII.

TABLE VIII

Conductimetric Measurements For The Oxyethylation Of Tribromophenol (× 100 Micromhos)

| CATALYST | 0 | 15 | 30 | 45 | 60 | 75 | 90 | 105 | 120 | 135 |
|---|---|---|---|---|---|---|---|---|---|---|
| Lithium Hydroxide | — | 14.0 | 14.0 | 14.0 | 13.4 | 13.5 | 12.7 | 13.2 | 13.6* | 20.5 |
| Sodium Hydroxide | — | — | — | —** | 8.5 | 11.0 | 18.5 | | | |
| Potassium Hydroxide | — | 17.5 | 17.0 | 16.5 | 16.0 | 16.0 | 15.5* | 24.0 | | |
| Lithium Methoxide | — | 14.5 | 14.4 | 14.0* | 21.0 | | | | | |
| Benzyltrimethyl-Ammonium Chloride | — | 21.0 | 21.0 | 18.0 | 17.5 | 17.0 | 16.5 | 16.5* | 25.5 | |

*Reaction End Point
**The reaction reached end point prior to circulation of the reactants through the conductimetric cell.

The conductance data for this Example V are plotted in FIG. 5. Once again the rapid increase in conductance signals reaction end point has been reached.

Reviewing the data presented in FIGS. 3–5 derived from the foregoing examples, it is noted that when reaction end point is reached, conductance of the reaction mixture rapidly increases. Thus, for the purposes of the in situ determination of the reaction end point of the oxyethylation of phenols, it is only necessary to measure the conductance of the reaction mixture and to note when conductance increases. Such increase signals the nearing of reaction end point. From a quantitative basis, the data establish that for the representative systems investigated herein, a conductance increase of at least 50 micromhos over a period of less than or equal to 5 minutes represents reaction end point. Accordingly, once such increase is noted, the reaction may be advantageously terminated.

While the present invention has been described with reference to an exemplary plant schematic and representative reactive systems and catalysts therefor, the invention should not be deemed limited thereto. Accordingly, certain modifications and changes to the present invention may be made by one skilled in the art while still falling within the scope and intent of the invention, and all such modifications and changes are deemed to be included herein.

I claim:

1. In a method for the reactive oxyethylation of phenols at temperatures in excess of 100° C., said reaction occurring in the presence of a catalyst, the improvement comprising:
   monitoring the oxyethylation reaction by repetitive in situ measurements of the conductance of representative samples of the reaction mixture; and
   terminating the reaction when the conductance measurements establish that the electrical conductivity of the reaction mixture significantly increases.

2. The method of claim 1 wherein the reaction is terminated when conductance of the reaction mixture increases at least 50 micromhos over a period of less than or equal to five minutes.

3. The method of claim 1 or 2, wherein said phenol is chosen from the group comprising hydroxybenzene, diphenol, halophenol, and halodiphenol and said catalyst is chosen from the group comprising an alkali metal hydroxide, a quaternary ammonium halide, and an alkali metal alkoxide.

4. The method of claim 3, wherein said catalyst is sodium hydroxide.

5. The method of claim 3, wherein said catalyst is potassium hydroxide.

6. The method of claim 3, wherein said catalyst is lithium hydroxide.

7. The method of claim 3, wherein said catalyst is benzyltrimethylammonium chloride.

8. The method of claim 3, wherein said catalyst is lithium methoxide.

9. The method of claim 3, wherein said halodiphenol is tetrabromobisphenol A.

10. The method of claim 3, wherein said diphenol is 1,4-dihydroxybenzene.

11. The method of claim 3, wherein said halophenol is 2,4,6-tribromophenol.

12. The method of claim 3, wherein said halophenol is 4-bromophenol.

13. The method of claim 3, wherein said diphenol is bisphenol A.

* * * * *

UNITED STATES PATENT AND TRADEMARK OFFICE
CERTIFICATE OF CORRECTION

PATENT NO. : 4,249,024
DATED : February 3, 1981
INVENTOR(S) : David C. Sanders

It is certified that error appears in the above—identified patent and that said Letters Patent is hereby corrected as shown below:

Column 3, line 32

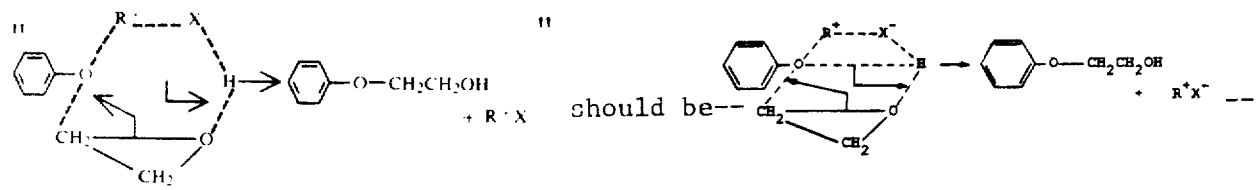

Column 3, line 59, "example." should be --example,--.

Column 4, line 11, "achieved" should be --achieved,--

*Signed and Sealed this*

*Eighth* Day of *November 1983*

[SEAL]

*Attest:*

GERALD J. MOSSINGHOFF

*Attesting Officer*   *Commissioner of Patents and Trademarks*